US006962977B2

United States Patent
Asano et al.

(10) Patent No.: US 6,962,977 B2
(45) Date of Patent: Nov. 8, 2005

(54) PROTEIN HAVING PESTICIDAL ACTIVITY, DNA ENCODING THE PROTEIN, AND NOXIOUS ORGANISM-CONTROLLING AGENT AND METHOD

(75) Inventors: Shinichiro Asano, Hokkaido (JP); Satoshi Yamanaka, Ibaraki (JP); Katsuyoshi Takeuchi, Ibaraki (JP)

(73) Assignee: SDS Biotech K.K., Tokyo (JP)

( * ) Notice: Subject to any disclaimer, the term of this patent is extended or adjusted under 35 U.S.C. 154(b) by 259 days.

(21) Appl. No.: 10/089,678

(22) PCT Filed: Aug. 2, 2001

(86) PCT No.: PCT/JP01/06660

§ 371 (c)(1),
(2), (4) Date: Apr. 3, 2002

(65) Prior Publication Data

US 2003/0017967 A1 Jan. 23, 2003

(30) Foreign Application Priority Data

Aug. 3, 2000 (JP) ......................................... 2000-236140

(51) Int. Cl.$^7$ ............................................... C07K 1/00
(52) U.S. Cl. ........................ 530/350; 530/300; 435/7.1; 435/69.1; 424/93; 424/93.2; 514/12; 514/2
(58) Field of Search .................................. 530/350, 300; 435/7.1, 69.1, 252.5; 424/93.2, 93; 514/12, 2

(56) References Cited

U.S. PATENT DOCUMENTS 5,554,534 A   9/1996   Michaels et al. ........ 435/252.3

FOREIGN PATENT DOCUMENTS

| EP | 498537 A | 8/1992 |
|----|----------|--------|
| JP | 06-065292 | 3/1994 |
| JP | 07-000179 | 1/1995 |
| JP | 08-228783 | 9/1996 |
| WO | WO 92/19106 A | 11/1992 |
| WO | WO 93/04587 A | 3/1993 |

OTHER PUBLICATIONS

Wells, Biochemistry, vol. 29, pp. 8509–8517, 1990.*
International Search Report.
Ryoichi Sato, et al., "Cloning, heterologous expression, and localization of a novel crystal protein gene from *Bacillus thurigiensus* serovar japonensis strain buibui toxic to scaarabaeid insects", Current Microbiology (1994), vol. 28, No. 1, pp. 15–19.
Patent Abstracts of Japan, JP–06–065292, dated Mar. 8, 1994.
Patent Abstracts of Japan, JP–07–000179, dated Jan. 6, 1995.
Patent Abstracts of Japan, JP08–228783, dated Sep. 10, 1996.

* cited by examiner

*Primary Examiner*—Jon Weber
*Assistant Examiner*—Hope Robinson
(74) *Attorney, Agent, or Firm*—Sughrue Mion, PLLC

(57) ABSTRACT

The invention provides a noxious organism-controlling agent effective to control pests that have acquired a resistance to conventional Bt agents, and which has activity on *Coleoptera* pests. Also, the invention provides a microbe, *Bacillus thuringiensis* serovar *galleriae* SDS502 strain, that produces a toxic protein. This toxic protein can serve as the active ingredient in a noxious organism-controlling composition. The invention provides a protein having pesticidal activity that is produced by the *Bacillus thuringiensis* serovar *galleriae* SDS502 strain, and a protein having an addition, deletion or substitution of a plurality of amino acids and having similar pesticidal activity. The invention also provides a DNA encoding protein having pesticidal activity, a microbe transformed with the DNA, and a plant transformed with the DNA and its seed.

5 Claims, 1 Drawing Sheet

SEQUENCE LISTING

<160> NUMBER OF SEQ ID NOS: 3

<210> SEQ ID NO 1
<211> LENGTH: 1167
<212> TYPE: PRT
<213> ORGANISM: Bacillus thuringiensis

<400> SEQUENCE: 1

```
Met Ser Pro Asn Asn Gln Asn Glu Tyr Glu Ile Leu Asp Ala Ser Ser
1               5                   10                  15

Ser Thr Ser Val Ser Asp Asn Ser Val Arg Tyr Pro Leu Ala Asn Asp
            20                  25                  30

Gln Thr Thr Thr Leu Gln Asn Met Asn Tyr Lys Asp Tyr Leu Arg Met
            35                  40                  45

Ser Glu Gly Glu Asn Pro Glu Leu Phe Gly Asn Pro Glu Thr Phe Ile
        50                  55                  60

Ser Ser Ser Thr Val Gln Thr Gly Ile Gly Ile Val Gly Gln Val Leu
65                  70                  75                  80

Gly Ala Leu Gly Val Pro Phe Ala Gly Gln Ile Ala Ser Phe Tyr Ser
                85                  90                  95

Phe Ile Val Gly Gln Leu Trp Pro Ser Ser Thr Val Ser Val Trp Glu
                100                 105                 110

Met Ile Met Lys Gln Val Glu Asp Leu Ile Asp Gln Lys Ile Thr Asp
            115                 120                 125

Ser Val Arg Lys Thr Ala Leu Ala Gly Leu Gln Gly Leu Gly Asp Gly
        130                 135                 140

Leu Asp Val Tyr Gln Lys Ser Leu Lys Asn Trp Leu Glu Asn Arg Asn
145                 150                 155                 160

Asp Thr Arg Ala Arg Ser Val Val Thr Gln Tyr Ile Ala Leu Glu
                165                 170                 175

Leu Asp Phe Val Ala Lys Ile Pro Ser Phe Ala Ile Ser Gly Gln Glu
            180                 185                 190

Val Pro Leu Leu Ser Val Tyr Ala Gln Ala Ala Asn Leu His Leu Leu
            195                 200                 205

Leu Leu Arg Asp Ala Ser Ile Phe Gly Ala Glu Trp Gly Phe Thr Pro
        210                 215                 220

Gly Glu Ile Ser Thr Phe Tyr Asp Arg Gln Val Thr Arg Thr Ala Gln
225                 230                 235                 240

Tyr Ser Asp Tyr Cys Val Lys Trp Tyr Asn Thr Gly Leu Asp Lys Leu
                245                 250                 255

Lys Gly Thr Asn Ala Ala Ser Trp Leu Lys Tyr His Gln Phe Arg Arg
                260                 265                 270

Glu Met Thr Leu Leu Val Leu Asp Leu Val Ala Leu Phe Pro Asn Tyr
            275                 280                 285

Asp Thr Arg Thr Tyr Pro Ile Glu Thr Thr Ala Gln Leu Thr Arg Glu
        290                 295                 300

Val Tyr Thr Asp Pro Ile Val Phe Asn Arg Glu Thr Ser Gly Gly Phe
```

-continued

```
                305                 310                 315                 320
Cys Arg Arg Trp Ser Leu Asn Ser Asp Ile Ser Phe Ser Glu Val Glu
                325                 330                 335

Ser Ala Val Ile Arg Ser Pro His Leu Phe Asp Ile Leu Ser Glu Ile
            340                 345                 350

Glu Phe Tyr Thr Thr Arg Ala Gly Leu Pro Leu Asn Thr Glu Tyr
            355                 360                 365

Leu Glu Tyr Trp Val Gly His Ser Ile Lys Tyr Lys Asn Thr Asn Ala
            370                 375                 380

Ser Ser Ala Leu Glu Arg Asn Tyr Gly Thr Ile Thr Ser Asn Lys Ile
385                 390                 395                 400

Lys Tyr Tyr Asp Leu Ala Asn Lys Asp Ile Phe Gln Val Arg Ser Leu
            405                 410                 415

Gly Ala Asp Leu Ala Asn Tyr Tyr Ala Gln Val Tyr Gly Val Pro Tyr
            420                 425                 430

Ala Ser Phe Thr Leu Leu Asp Lys Asn Thr Gly Ser Gly Ser Val Gly
            435                 440                 445

Gly Phe Thr Tyr Ser Lys Pro His Thr Thr Met Gln Val Cys Thr Gln
            450                 455                 460

Asn Tyr Asn Thr Ile Asp Glu Ile Pro Pro Glu Asn Glu Pro Leu Ser
465                 470                 475                 480

Arg Gly Tyr Ser His Arg Leu Ser His Ile Thr Ser Tyr Ser Phe Ser
                485                 490                 495

Lys Asn Ala Ser Ser Pro Ala Arg Tyr Gly Asn Leu Pro Val Phe Ala
            500                 505                 510

Trp Thr His Arg Ser Ala Asp Val Thr Asn Thr Val Tyr Ser Asp Lys
            515                 520                 525

Ile Thr Gln Ile Pro Val Val Lys Ala His Thr Leu Val Ser Gly Thr
            530                 535                 540

Thr Val Ile Lys Gly Pro Gly Phe Thr Gly Gly Asn Ile Leu Lys Arg
545                 550                 555                 560

Thr Ser Ser Gly Pro Leu Ala Tyr Thr Ser Val Ser Val Lys Ser Pro
                565                 570                 575

Leu Ser Gln Arg Tyr Arg Ala Arg Ile Arg Tyr Ala Ser Thr Thr Asn
            580                 585                 590

Leu Arg Leu Phe Val Thr Ile Ser Gly Thr Arg Ile Tyr Ser Ile Asn
            595                 600                 605

Val Asn Lys Thr Met Asn Lys Gly Asp Asp Leu Thr Phe Asn Thr Phe
            610                 615                 620

Asp Leu Ala Thr Ile Gly Thr Ala Phe Thr Phe Ser Asn Tyr Ser Asp
625                 630                 635                 640

Ser Leu Thr Val Gly Ala Asp Ser Phe Ala Ser Gly Gly Glu Val Tyr
                645                 650                 655

Val Asp Lys Phe Glu Leu Ile Pro Val Asn Ala Thr Phe Glu Ala Glu
            660                 665                 670

Glu Asp Leu Asp Val Ala Lys Lys Ala Val Asn Gly Leu Phe Thr Ser
            675                 680                 685

Lys Lys Asp Ala Leu Gln Thr Ser Val Thr Asp Tyr Gln Val Asn Gln
            690                 695                 700

Ala Ala Asn Leu Val Glu Cys Leu Ser Asp Glu Leu Tyr Pro Asn Glu
705                 710                 715                 720

Lys Arg Met Leu Trp Asp Ala Val Lys Glu Ala Lys Arg Leu Val Gln
            725                 730                 735
```

-continued

```
Ala Arg Asn Leu Leu Gln Asp Thr Gly Phe Asn Arg Ile Asn Gly Glu
        740                 745                 750

Asn Gly Trp Thr Gly Ser Thr Gly Ile Glu Val Ala Glu Gly Asp Val
        755                 760                 765

Leu Phe Lys Asp Arg Ser Leu Arg Leu Thr Ser Ala Arg Glu Ile Asp
        770                 775                 780

Thr Glu Thr Tyr Pro Thr Tyr Leu Tyr Gln Gln Ile Asp Glu Ser Leu
785                 790                 795                 800

Leu Lys Pro Tyr Thr Arg Tyr Lys Leu Lys Gly Phe Ile Gly Ser Ser
                805                 810                 815

Gln Asp Leu Glu Ile Lys Leu Ile Arg His Arg Ala Asn Gln Ile Val
                820                 825                 830

Lys Asn Val Pro Asp Asn Leu Leu Pro Asp Val Leu Pro Val Asn Ser
                835                 840                 845

Cys Gly Gly Ile Asp Arg Cys Ser Glu Gln Gln Tyr Val Asp Ala Asn
        850                 855                 860

Leu Ala Leu Glu Asn Asn Gly Glu Asn Gly Asn Met Ser Ser Asp Ser
865                 870                 875                 880

His Ala Phe Ser Phe His Ile Asp Thr Gly Glu Ile Asp Leu Asn Glu
                885                 890                 895

Asn Thr Gly Ile Trp Val Val Phe Lys Ile Pro Thr Thr Asn Gly Tyr
        900                 905                 910

Ala Thr Leu Gly Asn Leu Glu Leu Val Glu Glu Gly Pro Leu Ser Gly
        915                 920                 925

Glu Thr Leu Glu Arg Ala Gln Gln Gln Glu Gln Trp Gln Asp Lys
        930                 935                 940

Met Ala Arg Lys Arg Gly Ala Ser Glu Lys Ala Tyr Tyr Ala Ala Lys
945                 950                 955                 960

Gln Ala Ile Asp Arg Leu Phe Ala Asp Tyr Gln Asp Gln Lys Leu Asn
                965                 970                 975

Ser Gly Val Glu Met Ser Asp Met Leu Ala Ala Gln Asn Leu Val Gln
        980                 985                 990

Ser Ile Pro Tyr Val Tyr Asn Asp Ala Leu Pro Glu Ile Pro Gly Met
        995                 1000                1005

Asn Tyr Thr Ser Phe Thr Glu Leu Thr Asn Arg Leu Gln Gln Ala
        1010                1015                1020

Trp Asn Leu Tyr Asp Leu Arg Asn Ala Ile Pro Asn Gly Asp Phe
        1025                1030                1035

Arg Asn Gly Leu Ser Asp Trp Asn Ala Thr Ser Asp Val Asn Val
        1040                1045                1050

Gln Gln Leu Ser Asp Thr Ser Val Leu Val Ile Pro Asn Trp Asn
        1055                1060                1065

Ser Gln Val Ser Gln Gln Phe Thr Val Gln Pro Asn Tyr Arg Tyr
        1070                1075                1080

Val Leu Arg Val Thr Ala Arg Lys Glu Gly Val Gly Asp Gly Tyr
        1085                1090                1095

Val Ile Ile Arg Asp Gly Ala Asn Gln Thr Glu Thr Leu Thr Phe
        1100                1105                1110

Asn Ile Cys Asp Asp Asp Thr Gly Val Leu Ser Ala Asp Gln Thr
        1115                1120                1125

Ser Tyr Ile Thr Lys Thr Val Glu Phe Thr Pro Ser Thr Glu Gln
        1130                1135                1140
```

-continued

```
Val Trp Ile Asp Met Ser Glu  Thr Glu Gly Val Phe  Asn Ile Glu
    1145            1150              1155

Ser Val  Glu Leu Val Leu Glu  Glu Glu
    1160             1165

<210> SEQ ID NO 2
<211> LENGTH: 3504
<212> TYPE: DNA
<213> ORGANISM: Bacillus thuringiensis
<220> FEATURE:
<221> NAME/KEY: exon
<222> LOCATION: (1)..(3501)
<223> OTHER INFORMATION:

<400

-continued

```
                Tyr Ser Asp Tyr Cys Val Lys Trp Tyr Asn Thr Gly Leu Asp Lys Leu
                            245                 250                 255 aaa ggt acg aat gct gca agt tgg ctg aag tat cac caa ttc cga aga              816
Lys Gly Thr Asn Ala Ala Ser Trp Leu Lys Tyr His Gln Phe Arg Arg
                260                 265                 270 gaa atg aca tta ctg gta tta gat tta gta gcg tta ttt cca aac tat              864
Glu Met Thr Leu Leu Val Leu Asp Leu Val Ala Leu Phe Pro Asn Tyr
                275                 280                 285 gac aca cgt acg tat cca atc gaa aca acg gcc caa ctt aca cgg gaa              912
Asp Thr Arg Thr Tyr Pro Ile Glu Thr Thr Ala Gln Leu Thr Arg Glu
        290                 295                 300 gtg tat aca gat cca ata gta ttt aac aga gaa aca agt ggt gga ttt              960
Val Tyr Thr Asp Pro Ile Val Phe Asn Arg Glu Thr Ser Gly Gly Phe
305                 310                 315                 320 tgt agg cgt tgg tca ctt aac agt gat att tct ttt tca gaa gtc gaa             1008
Cys Arg Arg Trp Ser Leu Asn Ser Asp Ile Ser Phe Ser Glu Val Glu
                325                 330                 335 agc gct gta att cgt tca cca cac cta ttt gat ata ctc agt gaa ata             1056
Ser Ala Val Ile Arg Ser Pro His Leu Phe Asp Ile Leu Ser Glu Ile
                340                 345                 350 gaa ttt tat aca aca aga gcg ggg ctt ccc ttg aat aat acg gaa tac             1104
Glu Phe Tyr Thr Thr Arg Ala Gly Leu Pro Leu Asn Asn Thr Glu Tyr
                355                 360                 365 ctt gaa tat tgg gta gga cat tct ata aaa tat aaa aat acg aat gcc             1152
Leu Glu Tyr Trp Val Gly His Ser Ile Lys Tyr Lys Asn Thr Asn Ala
        370                 375                 380 tca tca gca tta gaa cgt aat tac ggt acg att act tct aac aaa atc             1200
Ser Ser Ala Leu Glu Arg Asn Tyr Gly Thr Ile Thr Ser Asn Lys Ile
385                 390                 395                 400 aag tat tat gat tta gca aat aag gat atc ttt cag gtt cga tca tta             1248
Lys Tyr Tyr Asp Leu Ala Asn Lys Asp Ile Phe Gln Val Arg Ser Leu
                405                 410                 415 ggg gcg gat tta gct aat tac tac gca cag gta tat gga gtt ccg tac             1296
Gly Ala Asp Leu Ala Asn Tyr Tyr Ala Gln Val Tyr Gly Val Pro Tyr
                420                 425                 430 gct agt ttt aca ctg ctt gac aag aat aca gga tca gga tca gtt gga             1344
Ala Ser Phe Thr Leu Leu Asp Lys Asn Thr Gly Ser Gly Ser Val Gly
                435                 440                 445 ggt ttt acg tac tca aaa cca cat aca act atg caa gta tgt aca caa             1392
Gly Phe Thr Tyr Ser Lys Pro His Thr Thr Met Gln Val Cys Thr Gln
        450                 455                 460 aat tac aat acg att gat gaa atc cct cca gag aat gag cca ctt agt             1440
Asn Tyr Asn Thr Ile Asp Glu Ile Pro Pro Glu Asn Glu Pro Leu Ser
465                 470                 475                 480 aga ggg tat agc cat aga tta tct cat atc acc tct tat tct ttt tct             1488
Arg Gly Tyr Ser His Arg Leu Ser His Ile Thr Ser Tyr Ser Phe Ser
                485                 490                 495 aag aat gct agt agt cct gct aga tat ggc aat ctc cct gta ttt gct             1536
Lys Asn Ala Ser Ser Pro Ala Arg Tyr Gly Asn Leu Pro Val Phe Ala
                500                 505                 510 tgg aca cat cgg agt gcg gat gtt aca aat aca gtt tat tca gat aaa             1584
Trp Thr His Arg Ser Ala Asp Val Thr Asn Thr Val Tyr Ser Asp Lys
                515                 520                 525 att act cag ata cca gtt gta aag gca cat act tta gtt tca ggt act             1632
Ile Thr Gln Ile Pro Val Val Lys Ala His Thr Leu Val Ser Gly Thr
        530                 535                 540 act gtt att aaa ggt cct gga ttt aca gga ggc aat atc ctt aaa aga             1680
Thr Val Ile Lys Gly Pro Gly Phe Thr Gly Gly Asn Ile Leu Lys Arg
545                 550                 555                 560
```

```
aca agt agt ggt ccg tta gct tat act agt gtc tct gta aaa tca cca         1728
Thr Ser Ser Gly Pro Leu Ala Tyr Thr Ser Val Ser Val Lys Ser Pro
            565                 570                 575 tta tca caa aga tat cgt gca aga ata cgt tat gct tct act act aac         1776
Leu Ser Gln Arg Tyr Arg Ala Arg Ile Arg Tyr Ala Ser Thr Thr Asn
            580                 585                 590 tta cga ctt ttt gta aca att tct gga act cgc att tac tct ata aat         1824
Leu Arg Leu Phe Val Thr Ile Ser Gly Thr Arg Ile Tyr Ser Ile Asn
            595                 600                 605 gtt aat aaa acc atg aat aaa ggg gat gat tta aca ttt aat aca ttt         1872
Val Asn Lys Thr Met Asn Lys Gly Asp Asp Leu Thr Phe Asn Thr Phe
            610                 615                 620 gac tta gca act att ggt act gct ttc aca ttt tca aat tac tcg gat         1920
Asp Leu Ala Thr Ile Gly Thr Ala Phe Thr Phe Ser Asn Tyr Ser Asp
625                 630                 635                 640 agc tta acg gta ggt gca gat tct ttt gct tca gga gga gaa gtt tat         1968
Ser Leu Thr Val Gly Ala Asp Ser Phe Ala Ser Gly Gly Glu Val Tyr
            645                 650                 655 gta gat aag ttc gaa ctt att ccg gta aat gca aca ttt gaa gca gaa         2016
Val Asp Lys Phe Glu Leu Ile Pro Val Asn Ala Thr Phe Glu Ala Glu
            660                 665                 670 gaa gac cta gat gtg gca aag aaa gca gta aat ggc ttg ttt acg agt         2064
Glu Asp Leu Asp Val Ala Lys Lys Ala Val Asn Gly Leu Phe Thr Ser
            675                 680                 685 aaa aaa gat gcc tta cag aca agt gta acg gat tat caa gtg aat caa         2112
Lys Lys Asp Ala Leu Gln Thr Ser Val Thr Asp Tyr Gln Val Asn Gln
            690                 695                 700 gcg gca aac tta gta gaa tgc cta tcc gat gag tta tac cca aat gaa         2160
Ala Ala Asn Leu Val Glu Cys Leu Ser Asp Glu Leu Tyr Pro Asn Glu
705                 710                 715                 720 aaa cga atg tta tgg gat gca gtg aaa gag gcg aaa cga ctt gtt cag         2208
Lys Arg Met Leu Trp Asp Ala Val Lys Glu Ala Lys Arg Leu Val Gln
            725                 730                 735 gca cgt aac tta ctc caa gat aca ggc ttt aat agg att aat gga gaa         2256
Ala Arg Asn Leu Leu Gln Asp Thr Gly Phe Asn Arg Ile Asn Gly Glu
            740                 745                 750 aac gga tgg acg gga agt acg gga atc gag gtt gcg gaa gga gat gtt         2304
Asn Gly Trp Thr Gly Ser Thr Gly Ile Glu Val Ala Glu Gly Asp Val
            755                 760                 765 ctg ttt aaa gat cgt tcg ctt cgt ttg aca agt gcg aga gag att gat         2352
Leu Phe Lys Asp Arg Ser Leu Arg Leu Thr Ser Ala Arg Glu Ile Asp
            770                 775                 780 aca gaa aca tat cca acg tat ctc tat caa caa ata gat gaa tca ctt         2400
Thr Glu Thr Tyr Pro Thr Tyr Leu Tyr Gln Gln Ile Asp Glu Ser Leu
785                 790                 795                 800 tta aaa cca tat aca aga tat aaa cta aaa ggt ttt ata gga agt agt         2448
Leu Lys Pro Tyr Thr Arg Tyr Lys Leu Lys Gly Phe Ile Gly Ser Ser
            805                 810                 815 caa gat tta gag att aaa tta ata cgt cat cgg gca aat caa atc gtc         2496
Gln Asp Leu Glu Ile Lys Leu Ile Arg His Arg Ala Asn Gln Ile Val
            820                 825                 830 aaa aat gta cca gat aat ctc ttg cca gat gta ctc cct gtc aat tct         2544
Lys Asn Val Pro Asp Asn Leu Leu Pro Asp Val Leu Pro Val Asn Ser
            835                 840                 845 tgt ggt ggg atc gat cgc tgc agt gag caa cag tat gta gac gcg aat         2592
Cys Gly Gly Ile Asp Arg Cys Ser Glu Gln Gln Tyr Val Asp Ala Asn
850                 855                 860 tta gca ctc gaa aac aat gga gaa aat gga aat atg tct tct gat tcc         2640
Leu Ala Leu Glu Asn Asn Gly Glu Asn Gly Asn Met Ser Ser Asp Ser
865                 870                 875                 880
```

-continued

```
cat gca ttt tct ttc cat att gat aca ggt gaa ata gat ttg aat gaa    2688
His Ala Phe Ser Phe His Ile Asp Thr Gly Glu Ile Asp Leu Asn Glu
            885                 890                 895 aat aca gga att tgg gtc gta ttt aaa att ccg aca aca aat gga tac    2736
Asn Thr Gly Ile Trp Val Val Phe Lys Ile Pro Thr Thr Asn Gly Tyr
900                 905                 910 gca aca cta gga aat ctt gaa ttg gta gaa gag ggg cca ttg tca ggg    2784
Ala Thr Leu Gly Asn Leu Glu Leu Val Glu Glu Gly Pro Leu Ser Gly
        915                 920                 925 gaa aca tta gaa cga gca caa caa caa gaa caa caa tgg caa gac aaa    2832
Glu Thr Leu Glu Arg Ala Gln Gln Gln Glu Gln Gln Trp Gln Asp Lys
    930                 935                 940 atg gca aga aaa cgt ggg gca tca gaa aaa gca tat tat gca gca aag    2880
Met Ala Arg Lys Arg Gly Ala Ser Glu Lys Ala Tyr Tyr Ala Ala Lys
945                 950                 955                 960 caa gcc att gat cgt tta ttc gca gat tat caa gac caa aaa ctt aat    2928
Gln Ala Ile Asp Arg Leu Phe Ala Asp Tyr Gln Asp Gln Lys Leu Asn
                965                 970                 975 tct ggt gta gaa atg tca gat atg ttg gca gcc caa aac ctt gta cag    2976
Ser Gly Val Glu Met Ser Asp Met Leu Ala Ala Gln Asn Leu Val Gln
            980                 985                 990 tcc att cct tac gta tat aat gat gcg tta cca gaa atc cct gga atg    3024
Ser Ile Pro Tyr Val Tyr Asn Asp Ala Leu Pro Glu Ile Pro Gly Met
        995                 1000                1005 aac tat acg agt ttt aca gag tta aca aat aga ctc caa caa gca       3069
Asn Tyr Thr Ser Phe Thr Glu Leu Thr Asn Arg Leu Gln Gln Ala
    1010                1015                1020 tgg aat ttg tat gat ctt cga aat gct ata cca aat gga gat ttt       3114
Trp Asn Leu Tyr Asp Leu Arg Asn Ala Ile Pro Asn Gly Asp Phe
1025                1030                1035 cga aat gga tta agt gat tgg aat gca aca tca gat gtg aat gtg       3159
Arg Asn Gly Leu Ser Asp Trp Asn Ala Thr Ser Asp Val Asn Val
    1040                1045                1050 caa caa cta agc gat aca tct gtc ctt gtc att cca aac tgg aat       3204
Gln Gln Leu Ser Asp Thr Ser Val Leu Val Ile Pro Asn Trp Asn
1055                1060                1065 tct caa gtg tca caa caa ttt aca gtt caa ccg aat tat aga tat       3249
Ser Gln Val Ser Gln Gln Phe Thr Val Gln Pro Asn Tyr Arg Tyr
    1070                1075                1080 gtg tta cgt gtc aca gcg aga aaa gag gga gta gga gac gga tat       3294
Val Leu Arg Val Thr Ala Arg Lys Glu Gly Val Gly Asp Gly Tyr
1085                1090                1095 gtg atc atc cgt gat ggt gcg aat cag aca gaa aca ctc aca ttt       3339
Val Ile Ile Arg Asp Gly Ala Asn Gln Thr Glu Thr Leu Thr Phe
    1100                1105                1110 aat ata tgt gat gat gat aca ggt gtt tta tct gct gat caa act       3384
Asn Ile Cys Asp Asp Asp Thr Gly Val Leu Ser Ala Asp Gln Thr
1115                1120                1125 agc tat atc aca aaa aca gtg gaa ttc act cca tct aca gag caa       3429
Ser Tyr Ile Thr Lys Thr Val Glu Phe Thr Pro Ser Thr Glu Gln
    1130                1135                1140 gtt tgg att gac atg agt gag acc gaa ggt gta ttc aac ata gaa       3474
Val Trp Ile Asp Met Ser Glu Thr Glu Gly Val Phe Asn Ile Glu
1145                1150                1155 agt gta gaa ctc gtg tta gaa gaa gag taa                           3504
Ser Val Glu Leu Val Leu Glu Glu Glu
    1160                1165
```

<210> SEQ ID NO 3

<211> LENGTH: 3690
<212> TYPE: DNA
<213> ORGANISM: Bacillus thuringiensis

<400> SEQUENCE: 3

| | | | | | |
|---|---|---|---|---|---|
| gaattctaat | gacacagtag | aatattttta | aaataaagat | ggaaggggggg | atatgaaaaa         60 |
| tataatcaca | agagtcatac | aaaaagatgg | ttatgttaaa | acaaaaaaat | cctgtaggaa        120 |
| taagggttta | aaagcaatcg | tttgaaaaga | tagttatatt | aaattgtatg | tatagggggga       180 |
| aaaaagatga | gtccaaataa | tcaaaatgaa | tatgaaattc | tagatgcttc | atcatctact       240 |
| tctgtatccg | ataattctgt | tagatacccct | ttagcaaacg | atcaaacgac | acattacaa        300 |
| aacatgaact | ataagagatta | tctgagaatg | tctgagggag | agaatcctga | attatttgga       360 |
| aatccggaga | cgtttattag | ttcatctacg | gttcaaactg | gaattggcat | tgttggtcaa       420 |
| gtactggggg | ctttagggggt | tccatttgct | ggacagatag | ctagttttta | tagtttcatt       480 |
| gtcggtcaat | tatggccatc | aagtaccgtg | agtgtatggg | aaatgattat | gaaacaagtg       540 |
| gaagatctaa | ttgatcaaaa | ataacagat | tctgtaagga | aaacagcgct | tgcaggacta       600 |
| caaggattag | gagatggctt | agacgtatat | cagaaatcac | ttaagaattg | gctggaaaat       660 |
| cgtaatgata | caagagctag | aagtgttgtg | gtgacccaat | atatagcttt | agagcttgat       720 |
| tttgttgcta | aaatcccatc | ttttgcaata | tctggacagg | aagtaccatt | attatcagtg       780 |
| tatgcacaag | cagcgaattt | acatttgcta | ttattacgag | atgcttccat | ttttggagca       840 |
| gagtggggat | tcacaccagg | agaaatttcc | acatttatg  | atcgtcaggt | gacacgtacc       900 |
| gcccaatact | cggattattg | tgtaaagtgg | tataacactg | gcttagataa | attaaaaggt       960 |
| acgaatgctg | caagttggct | gaagtatcac | caattccgaa | gagaaatgac | attactggta      1020 |
| ttagatttag | tagcgttatt | tccaaactat | gacacacgta | cgtatccaat | cgaaacaacg      1080 |
| gcccaactta | cacgggaagt | gtatacagat | ccaatagtat | ttaacagaga | aacaagtggt      1140 |
| ggattttgta | ggcgttggtc | acttaacagt | gatatttctt | tttcagaagt | cgaaagcgct      1200 |
| gtaattcgtt | caccacacct | atttgatata | ctcagtgaaa | tagaattta  | tacaacaaga      1260 |
| gcggggcttc | ccttgaataa | tacggaatac | cttgaatatt | gggtaggaca | ttctataaaa      1320 |
| tataaaaata | cgaatgcctc | atcagcatta | gaacgtaatt | acggtacgat | tacttctaac      1380 |
| aaaatcaagt | attatgattt | agcaaataag | gatatctttc | aggttcgatc | attagggggcg      1440 |
| gatttagcta | attactacgc | acaggtatat | ggagttccgt | acgctagttt | tacactgctt      1500 |
| gacaagaata | caggatcagg | atcagttgga | ggttttacgt | actcaaaacc | acatacaact      1560 |
| atgcaagtat | gtacacaaaa | ttacaatacg | attgatgaaa | tccctccaga | gaatgagcca      1620 |
| cttagtagag | ggtatagcca | tagattatct | catatcacct | cttattcttt | ttctaagaat      1680 |
| gctagtagtc | ctgctagata | tggcaatctc | cctgtatttg | cttggacaca | tcggagtgcg      1740 |
| gatgttacaa | atacagttta | ttcagataaa | attactcaga | taccagttgt | aaaggcacat      1800 |
| actttagttt | caggtactac | tgttattaaa | ggtcctggat | tacaggagg  | caatatcctt      1860 |
| aaaagaacaa | gtagtggtcc | gttagcttat | actagtgtct | ctgtaaaatc | accattatca      1920 |
| caaagatatc | gtgcaagaat | acgttatgct | tctactacta | acttacgact | ttttgtaaca      1980 |
| atttctggaa | ctcgcattta | ctctataaat | gttaataaaa | ccatgaataa | agggggatgat      2040 |
| ttaacattta | atacatttga | cttagcaact | attggtactg | ctttcacatt | ttcaaattac      2100 |
| tcggatagct | taacggtagg | tgcagattct | tttgcttcag | gaggagaagt | ttatgtagat      2160 |
| aagttcgaac | ttattccggt | aaatgcaaca | tttgaagcag | aagaagacct | agatgtggca      2220 |

```
aagaaagcag taaatggctt gtttacgagt aaaaaagatg ccttacagac aagtgtaacg    2280
gattatcaag tgaatcaagc ggcaaactta gtagaatgcc tatccgatga gttataccca    2340
aatgaaaaac gaatgttatg ggatgcagtg aaagaggcga aacgacttgt tcaggcacgt    2400
aacttactcc aagatacagg ctttaatagg attaatggag aaaacggatg gacgggaagt    2460
acgggaatcg aggttgcgga aggagatgtt ctgtttaaag atcgttcgct tcgtttgaca    2520
agtgcgagag agattgatac agaaacatat ccaacgtatc tctatcaaca aatagatgaa    2580
tcacttttaa aaccatatac aagatataaa ctaaaaggtt ttataggaag tagtcaagat    2640
ttagagatta aattaatacg tcatcgggca aatcaaatcg tcaaaaatgt accagataat    2700
ctcttgccag atgtactccc tgtcaattct tgtggtggga tcgatcgctg cagtgagcaa    2760
cagtatgtag acgcgaattt agcactcgaa aacaatggag aaaatggaaa tatgtcttct    2820
gattcccatg cattttcttt ccatattgat acaggtgaaa tagatttgaa tgaaaataca    2880
ggaatttggg tcgtatttaa aattccgaca acaaatggat acgcaacact aggaaatctt    2940
gaattggtag aagaggggcc attgtcaggg gaaacattag aacgagcaca acaacaagaa    3000
caacaatggc aagacaaaat ggcaagaaaa cgtggggcat cagaaaaagc atattatgca    3060
gcaaagcaag ccattgatcg tttattcgca gattatcaag accaaaaact taattctggt    3120
gtagaaatgt cagatatgtt ggcagcccaa aaccttgtac agtccattcc ttacgtatat    3180
aatgatgcgt taccagaaat ccctggaatg aactatacga gttttacaga gttaacaaat    3240
agactccaac aagcatggaa tttgtatgat cttcgaaatg ctataccaaa tggagatttt    3300
cgaaatggat taagtgattg gaatgcaaca tcagatgtga atgtgcaaca actaagcgat    3360
acatctgtcc ttgtcattcc aaactggaat tctcaagtgt cacaacaatt tacagttcaa    3420
ccgaattata gatatgtgtt acgtgtcaca gcgagaaaag agggagtagg agacggatat    3480
gtgatcatcc gtgatggtgc gaatcagaca gaaacactca catttaatat atgtgatgat    3540
gatacaggtg ttttatctgc tgatcaaact agctatatca caaaaacagt ggaattcact    3600
ccatctacag agcaagtttg gattgacatg agtgagaccg aaggtgtatt caacatagaa    3660
agtgtagaac tcgtgttaga agaagagtaa                                    3690
```

PROTEIN HAVING PESTICIDAL ACTIVITY, DNA ENCODING THE PROTEIN, AND NOXIOUS ORGANISM-CONTROLLING AGENT AND METHOD

This application is a 371 of PCT/JP01/06660, filed Aug. 2, 2001, which claims priority to JP 2000-236140 filed Aug. 3, 2000.

TECHNICAL FIELD

The present invention relates to a protein having a pesticidal activity, DNA encoding the protein, a noxious organism-controlling agent and -controlling method as well as to a novel *Bacillus thuringiensis serovar galleriae* SDS502 strain (hereinafter, sometimes abbreviated as SDS502).

BACKGROUND ART

*Bacillus thuringiensis* (hereinafter, sometimes abbreviated as Bt) forms endospores like other *Bacillus* bacteria. The spores germinate and grow into vegetative cells in the presence of suitable nutritional components. The vegetative cells repeat cell division successively and sooner or later turn into sporangia that form endospores and crystal protein in the cells due to exhaustion of nutritional components, environmental changes, and so forth. Further, the cells are destructed to release the endospores and crystal protein.

Insects eat the spores and crystal protein Bt produces. When they reach the mesenteron in the digestive tract, the protein is dissolved under strongly alkaline conditions of the digestive juice to produce a protoxin, which then is converted by a proteolytic enzyme into an active ingredient (toxin). The active ingredient binds to a receptor in an epithelial cell of the mesenteron to injure cells in the vicinity of it. In the injured part, the digestive juice and the body fluid mix with each other to change the osmotic pressure and pH in the body. As a result, the food digesting function is disturbed, paralysis of mouth-part is caused, and the feeding action is retarded in the insect. Furthermore, the spores germinate under nutritional conditions and they invade into the hemocele of the insect as the vegetative cells propagate, thus causing blood poisoning.

Although insects may have different sensitivity depending on the species of insect, usually the feeding action ceases after several hours and the insect dies after 2 or 3 days after eating Bt. It is attributable to this phenomenon that less damage by insects' eating is observed even when some insects remain alive after Bt is used. Many synthetic insecticides act on the nerve system of insect so that vigorous convulsion or knockdown effect, paralysis or the like phenomenon is observed. However, the mechanism of the action of Bt is quite different as described above and the effect is gradually exhibited even though living insects exist after the treatment. Bt and protein having a pesticidal activity (crystalline toxic protein) produced by Bt are very useful as an environmentally safe microbial pesticides (Bt agents), in particular as insecticides for *Lepidoptera* insects and are practically used worldwide.

Bt is gram-positive rod cells and produces crystal protein in the spore formation stage at a late stage of logarithmic phase. The crystal protein is not converted into a protein having a pesticidal activity to cause gut paralysis and systemic paralysis before it is orally taken into the digestive tract by an insect to be subjected to alkali decomposition and enzymatic decomposition in the digestive juice. However, it does not exhibit toxicity to mammals.

The crystal proteins Bt produces are formed in the sporangium along with the spores and released to the outside of the cell together with the spores after passing the phase of the sporangium (Nature, 172, 1004, 1953). These generally constitute complex crystals such as diamond-shaped, bipyramidal, rhomboidal and so forth and are insoluble in water. They are produced one per spore at the time of spore formation and released together with spores into medium as the bacterial cell is destructed. Usually they are of a steric rhombic or orthorhombic structure and have a size on the order of 2.0 $\mu$ in the long side and 0.6 $\mu$ in the short side. Subspecies include also amorphous ones and their size varies widely. On their surface, regular stripe structures can be seen. Isolation from the medium and purification of crystal protein can be performed by use of a bilayer fractionation method, a density gradient centrifugation method or the like.

The crystal proteins are soluble in an NaOH solution having a pH 12 or more. According to the analyses by SDS-PAGE (polyacrylamide gel electrophoresis), there are observed three proteins of about 130 to 135 kDa, about 65 kDa and about 80 kDa in a bacterial strain belonging to *Bacillus thuringiensis*. They are generically called Cry 1 protein, Cry 2 protein, and Cry 5 protein. Furthermore, they can be separated into a plurality of proteins that have almost approximate molecular weights but partially differ from each other by a fractionation operation such as high performance liquid chromatography. That is, in the case of Cry-1 protein, it is classified into proteins Cry-1Aa, Cry1Ab and so forth.

Bt was isolated from larva of Mediterranean flour moth (*Ephestia kuehniella* Zeller [Pyralidae]) by Berliner, a German researcher in 1911. Since the larva of the insect ate the flour from Thuringia, the insect was named *Thuringiensis*. Earlier than this, Dr. Ishiwatari isolated the same bacterial species as a pathogenic bacterium to silkworm in 1901. Thus, it is understood that Bt has widely occurred in the natural world since old. For example, it is present in grain warehouses and millhouses where grain pests inhabit. Also, it is detected in wagons and cabins and so forth for transporting grains. Thus it is known that it migrates everywhere in the world. Also in Japan, its distribution in every district has been examined and many *Bacillus thuringiensis* strains have been isolated from the dust in the houses of silkworm farmers, the surface of plants and so forth.

The bacteria that belong to the genus *Bacillus* amount to 70 or more species. Those strains frequently observed worldwide include 22 strains. They are distinguished basically by the ability of spore formation and shape of spore, production of gas, production of acetylmethylcarbinol (AMC), reduction of nitrates, and assimilability of some sugars in accordance with the techniques of Thiery and Franchon. *Bacillus thuringiensis* (*B. thuringiensis*) is finally distinguished from its allied species by the presence or absence of a crystal having a pesticidal activity ("Manual of techniques in insect pathology," L. Lacey ed., Academic Press, California, 55–77 (1997)).

The characteristics used for distinguishing *Bacillus thuringiensis* from other bacterial species and other species belonging to the genus *Bacillus* include gram-positive rod, catalase (+), spore formation (+), ovary spore, 0.9 $\mu$ or more in width of vegetative cell, production of acetylmethylcarbinol (+), facultative anaerobicity, assimilation of D-mannitol (−), and existence of crystal protein (+).

For the identification of subspecies of Bt, flagellum antigen (H-antigen) according to the serological technique by De Barjac and Bonefoi using an antibody in a rabbit serum to the flagellum of a bacterium has been employed for a long time as long as 40 years (Entomophaga 7, 5–31, 1962). This is a technique that has been widely utilized for the phylogenetic systematics of *Bacillus thuringiensis*.

The pesticidal activity of the bacterial strains varies depending on subspecies and is of an extremely high specificity. For example, there have been known *kurustaki, aizawai* and so forth as subspecies that exhibit an activity to *Lepidoptera* insects and *tenebrionis, japonensis* and so forth as subspecies that exhibit an activity to *Coleoptera* insects.

However, in actuality, bacterial strains belonging to the same subspecies may differ in the spectrum of pesticidal activity depending on the strain. In the case of Bt strains that have an activity to a part of *Lepidoptera* insect pests, the pests have acquired a resistance thereto. In addition, few reports have been made on strains exhibiting effective activity to *Coleoptera* insects.

Thus, a novel Bt agent that is effective to *Lepidoptera* insect pests having acquired a resistance to the Bt agent is demanded. Furthermore, there is a keen demand for a Bt agent having an activity to *Coleoptera* insects. Among these, novel Bt agents having a pesticidal activity to larvae of *Coleoptera* insects, in particular larvae of scarabs, thus far reported include only *Bacillus thuringiensis Serovar, japonensis* strain *buibui*) strain (Japanese Patent Application Laid-open Nos. Hei 6-65292 and Hei 7-179) and *Bacillus thuringiensis* var. *japonensis* N141 (Japanese Patent Application Laid-open No. Hei 8-228783).

DISCLOSURE OF THE INVENTION

The conventional *buibui* strain or N141 strain belonging to the subspecies *japonensis* does not exhibit sufficient effect on larvae of scarabs, in particular larvae of *Anomala cuprea*, a serious pest for lawn grasses, taro, sweet potato, peanut and so forth, and *Anomala orientalis* and *Popillia japonica*, pests for lawn grasses. Furthermore, Bt toxins of the microbe that belongs to the same bacterial species (subspecies) exhibit crossing in case a resistance is developed in a part thereof, with the result that its effect is considerably decreased. On the other hand, Bt toxins take a certain time for their effect to be exhibited. Therefore, discovery of a novel toxin that has a more potent pesticidal activity is keenly desired.

Therefore, an object of the present invention is to provide a novel bacterial strain belonging to *Bacillus thuringiensis serovar galleriae* that produces a pesticidal protein having a high pesticidal activity to larvae of *Coleoptera* insects and to provide a protein having a pesticidal activity derived from the novel microbe.

Furthermore, an object of the present invention is to provide a protein that has the above pesticidal activity, a protein that has an amino acid sequence obtained by addition, deletion or substitution of a plurality of amino acids in the amino acid sequence that constitutes the protein and has the same pesticidal activity, DNAs that encode such amino acid sequences, microbes that have been transformed by use of the DNAs and produce proteins having pesticidal activity, plants transformed by use of such DNAs or seeds thereof, and noxious organism-controlling agents and -controlling methods.

DETAILED DESCRIPTION OF THE INVENTION

Figure 1:
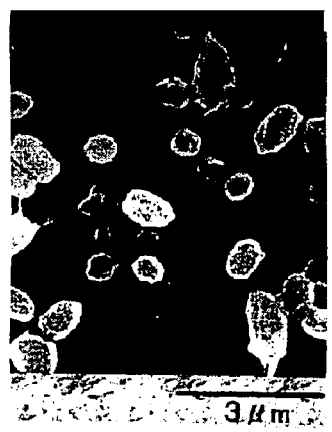
FIG. 1 is an electron micrograph of *Bacillus thuringiensis serovar galleriae* SD502 strain.

With a view to finding out a novel microbe having a high effect on larvae of *Coleoptera* insects, the present inventors have conducted repeated analyses and as a result they have isolated a *Bacillus thuringiensis serovar galleriae* SD502 strain belonging to *Bacillus thuringiensis serovar galleriae* that produces a pesticidal protein having a high pesticidal activity to larvae of *Coleoptera* insects. Thus, they have achieved the present invention that relates to a pesticide containing the novel *Bacillus thuringiensis serovar galleriae* SD502 itself and/or a pesticidal protein (toxic protein) it produces as active ingredient(s).

Furthermore, they have confirmed that a DNA encoding the pesticidal protein the novel microbe of the present invention produces, a protein having an amino acid sequence encoded by the DNA, and a noxious organism-controlling agent containing the protein as an active ingredient are effective as pest-controlling means and thus achieved the present invention.

That is, the present invention relates to (1) proteins having a pesticidal activity, (2) DNA encoding such proteins, (3) noxious organism-controlling agents, (4) plant protecting methods, (5) (5-1) microbes, (5-2) plants or seeds thereof transformed by use of the DNA, and (6) novel microbe, as set forth below.

A protein having an amino acid sequence described in SEQ ID NO:1 in the Sequence Listing and exhibiting a pesticidal activity.

A protein having an amino acid sequence derived by addition, deletion or substitution of a plurality of amino acids in the amino acid sequence described in SEQ ID NO:1 in the Sequence Listing and exhibiting a pesticidal activity.

A DNA containing a nucleotide sequence encoding the protein as described in 1) above.

The DNA as described in 3) above, containing a nucleotide sequence as described in SEQ ID NO:3 in the Sequence Listing.

A DNA containing a nucleotide sequence encoding the protein as described in 2) above.

A noxious organism-controlling agent, comprising a microbe producing a protein having an amino acid sequence described in SEQ ID NO:1 in the Sequence Listing, selected from (1-1) *Bacillus thuringiensis serovar galleriae* SD502 strain, (1-2) a mutant thereof, and (1-3) a microbe transformed with a DNA containing a nucleotide sequence encoding a protein having an amino acid sequence described in SEQ ID NO:1 in the Sequence Listing, or a protein having a pesticidal activity, produced by a microbe selected from (2-1) the above-mentioned SDS502 strain, (2-2) its mutant, and (2-3) transformed microbe.

A microbe transformed with the DNA as described in 5) above and producing a protein exhibiting a pesticidal activity as described in 2) above.

A plant transformed with the DNA as described in 3) or 5) above, or seed thereof.

A method for controlling a noxious organism, wherein the protein as described in 1) or 2) above is fed to a noxious organism to protect a plant from damage caused by the noxious organism.

The method for controlling a noxious organism as described in 9) above, wherein the noxious organism is a *Coleoptera* insect and the plant is protected from damage caused by the noxious organism.

*Bacillus thuringiensis serovar galleriae* SDS502 strain producing a protein having an amino acid sequence described in SEQ ID NO:1 in the Sequence Listing and exhibiting a pesticidal activity.

Novel *Bacillus thuringiensis serovar galleriae* SDS502 strain of the present invention has been internationally deposited at National Institute of Advanced Industrial Science and Technology, Independent Administrative Institution, under Accession No. FERM BP-7667.

The SDS502 strain can be cultured in a medium in which general bacteria can grow by a common fermentation technique.

Examples of medium include a common broth medium (0.3% of meat extract, 1.0% of peptone, and 0.5% of NaCl, pH 7.0), an MBS medium (0.7% of $KH_2PO_4$, 1% of bactotryptose, 0.2% of yeast extract, 0.03% of $MgSO_4 \cdot 7H_2O$, and 0.02% of $CaCl_2 \cdot 2H_2O$, pH 7.2), an MRVP medium (0.5% of polypeptone, 0.5% of glucose, and 0.5% of NaCl, pH 7.0) and so forth.

As the carbon source, glucose, fructose, saccharose, maltose, molasses, soluble starch, cornstarch and so forth may be utilized.

As the nitrogen source, ammonium chloride, ammonium sulfate, urea, yeast extract, peptone, soybean powder, cascin and so forth may be utilized.

Furthermore, it is preferable that as other inorganic salts and vitamins, $NaH_2PO_4$, $K_2HPO_4$, $MnSO_4$, $FeSO_4$, $MgSO_4$, NaCl, molasses, yeast extract, EBIOS (vitamin preparation) and so forth be added. The pH is preferably 6 to 8. The incubation temperature is preferably 25 to 33° C. The incubation time is preferably 24 to 120 hours. The culture method is preferably the one under aerobic conditions, such as aerobic spinner culture.

In the case where pesticidal crystal protein is isolated from the culture broth after the incubation, a common centrifugal separation method, a filtration method and so forth may be utilized. Alternatively, the SDS502 strain and/or crystal protein the SDS502 strain produces may be used in the form of a mixture with vegetative cells and/or spores without separation therefrom.

Also, mutant strains that produce a pesticidal crystal protein may be obtained from the SDS502 strain as an original strain by spontaneous or induced mutation, which strains may be used as an insecticidal crystal protein-producing strain according to the present invention. As the method for making mutant strains, a common method conventionally known can be used, for example, a method in which an original strain is subjected to artificial mutation by irradiation of ultraviolet rays or with a chemical such as N-methyl-N'-nitro-N-nitrosoguanidine (NTG), spread on an agar medium containing skimmed milk, screening a colony forming a greater clear zone around the colony from among the strains that grow thereon, and screening a strain having an excellent productivity.

In the case where a noxious organism-controlling agent containing the SDS502 strain and/or SDS502 crystal protein as an active ingredient or ingredients, it may be made into an optional formulation such as wettable powder, granules, dust, flowable formulation in the same manner as in common pesticides. These are used in admixture with a suitable carrier for respective formulations, for example, powder of a mineral such as agalmatolite, talc, kaolin, calcium carbonate, bentonite, silica stone powder, limestone powder, acid clay, diatomaceous earth powder, gypsum, pumice powder, shell powder, mica powder, or colloidal hydrated sodium silicate, water, or aqueous solutions such as buffer solutions. Preferably, they are used after addition of a fixing agent such as an alkylbenzenesulfonate or an alkylsulfonate, a humectant such as a polyoxyethylene (POE) alkyl ether, a POE alkyl phenyl ether, a POE dialkyl phenyl ether, a POE alkylamine or a dialkyl sulfosuccinate, a dispersing agent such as an alkyl sulfate, a POE alkyl ether sulfate, a POE alkyl phenyl ether sulfate, a POE benzylated (or salicylated) phenyl (or phenylphenyl) ether sulfate, a paraffin (alkane) sulfonate, an alpha-olefin sulfonate (AOS), an alkyl benzenesulfonate, a mono- or dialkyl naphthalene sulfonate, a naphthalenesulfonate/formaldehyde condensate, an alkyl diphenyl ether disulfonate, a lignin sulfonate, a POE alkyl ether sufosuccinate half ester, or a POE benzyl (or styrylated) phenyl (or phenylphenyl) ether phosphate, a mildewproofing agent such as a paraoxybenzoic acid derivative, salicyl anilide, 1,2-benzoisothiazolin-3-one, tetraphthalonitrile (TPN) or 2-nitrobromo compound.

In contrast to using the SDS502 strain and/or SDS502 strain-produced crystal protein as a single active ingredient, it is also possible to mix it with herbicides, various pesticides, bactericides or plant growth regulators which are effective to other noxious organisms, synergists for multiplying the effect, attractants as well as plant nutritive agents, fertilizers and so forth that are intended to obtain other functions.

In preparing a noxious organism-controlling agent containing the SDS502 strain and/or SDS502 strain-produced crystal protein as an active ingredient or ingredients, its active ingredient content is suitably on the order of 10 to 99%, preferably 40 to 90%. However, the active ingredient content may be adjusted depending on the target noxious organism, cultivated crop, method of use, time of use and so forth.

The crystal protein of the present invention includes, in addition to those having the amino acid sequence as described in SEQ ID NO:1 in the Sequence Listing, also those having the one that is partly deficient (for example, a polypeptide composed of only a portion that is necessary for the expression of bioactivity out of the amino acid sequence as described in SEQ ID NO:1 in the Sequence Listing), those having the one partly substituted with other amino acids (for example, the one substituted by amino acids having similar physical properties), and those in which other amino acids are added or inserted in some part thereof.

As is well known in the art, 1 to 6 kinds of codon are known to code for one amino acid (for example, one kind for Met and 6 kinds for Leu). Therefore, the nucleotide sequence of DNA can be altered without altering the amino acid sequence of a polypeptide.

Examples of the pests that can be controlled by the method of the present invention include the following

*Coleoptera* insects. That is, scarabs such as *Anomala cuprea, Anomala diversa, Anomala octiescostata, Hoplia communis, Ectinohoplia obducta, Anomala orientalis, Anomala osakana, Anomala testaceipes, Anomala schonfeldti, Anomala rufocuprea, Anomala albopilosa, Maladera castanea, Melolontha japonica, Adoretus tenuimaculatus* and *Popillia japonica*, ladybugs such as *Epilachna vigintioctopunctatav* and *Epilachna vigintioctomaculata*, weevils such as *Lissorhoptrus oryzophilus, Scepticus griseus, Cylas formicarius, Sphenophrus venatus vestius* and *Sitophilus zeamaise*, leaf beetles such as *Phyllotreta striolata* and *Aulacophora femoralis*, click beetle such as *Melanotus okinawaensis*, long-horned beetles such as *Monochamus alternatus* and *Mesosa myops*, bark beetles such as *Scolytus japonicus* and *Xylosandrus germanus*, and confused flour beetles such as *Tenebrio molitor* and *Tribolium castaneum*.

The method for controlling a noxious organism of the present invention using a noxious organism-controlling agent that contains the SDS502 strain and/or SDS502 crystal protein as an active ingredient or ingredients can be used for protecting a wide variety of plants that are susceptible to attack of *Coleoptera* insect pests. Specific examples of target plant include vegetables such as Chinese cabbage and cabbage, fruit vegetables such as cauliflower, root crop such as sweet potato or taro, citrus, defoliating fruit trees, cereals such as rice, wheat and beans, lawn grass in golf courses, gardens and so forth, specialty crop such as tea or sugarcane, stored cereals, stored food and flower trees. Also, the method of the present invention can be used for trees in forestation and non-agricultural areas such as parks, trees in forests, and seedling and so forth.

Generally, the method for protecting plants from insect damages by *Coleoptera* insect pests by use of a noxious organism-controlling agent that contains the SDS502 strain and/or SDS502 crystal protein as an active ingredient or ingredients can be practiced by treating (for example, spraying on) a plant where insect pests proliferate or will tend to proliferate with a composition of the above-mentioned noxious organism-controlling agent diluted with a diluent such as water, or directly mixing or injecting into soil without dilution.

The SDS502 gene can be isolated from the SDS502 strain. Total DNA of the SDS502 strain is digested with one or more restriction enzymes and the produced DNA fragment is converted to a 2- to 5-kbp DNA fraction. The fraction is linked to a suitable vector and *Escherichia coli* is transformed therewith. Next, using an antibody to the pesticidal crystal protein the SDS502 strain produces, an enzyme immunoassay method is practiced and thus an *Escherichia coli* transformant having the objective gene can be obtained.

The crystal protein gene DNA derived from the SDS502 strain thus obtained is treated with a suitable restriction enzyme or enzymes and the obtained DNA fragment is coupled to a suitable cloning vector to make a gene cassette. Using this, microbes such as *Escherichia coli* and *Bacillus subtilis* can be transformed. For example, *Escherichia coli* can be transformed and a nucleotide sequence encoding the SDS502 strain produced crystal protein can be analyzed by a gene analysis method such as a dideoxy method.

Using the gene cassette, gram-positive bacteria having a pesticidal activity, for example, *Bacillus thuringiensis serovar galleriae* or other subspecies can be transformed. This enables one to obtain transformed *Bacillus thuringiensis* effective for controlling a broader range of insects.

Furthermore, to express the SDS502 gene in plants, a preferred restriction site may be introduced so as to be located on a flank of each gene or gene part to induce mutation of a specified site.

The SDS502 gene part encoding the active part of the pesticidal crystal protein of the SDS502 strain can be stably inserted in the nuclear genome in a single plant cell to make a transformed plant having a resistance to insects or having the ability of killing insects.

As a result, using the obtained transformed plant, transformed plants having the same characteristics can be produced. Furthermore, the SDS502 gene part having a resistance to insects or the ability of killing insects can be introduced into other variants of the same or related plant species. The seeds obtained from the transformed plants are stable genome inserted products that contain the SDS502 gene part that can exhibit a resistance to insects or insecticidal activity and that is effective as a pesticide.

The SDS502 strain may be further transformed with one or more exogenous Bt genes having pesticidal activities. For example, the noxious organisms on which the SDS502 strain and/or SDS502 strain-produced crystal protein has no activity includes in particular larvae of *Lepidoptera* insects. Now, a chimera gene of the SDS502 gene with a gene encoding a crystal protein derived from other microbe exhibiting an effective activity on them may be prepared and used for transforming the microbe to the one having a wider pesticidal spectrum. By so doing, transformed SDS502 strains that can control a wider variety of pests are produced.

Antibody specific to SDS502 strain crystal protein can be prepared by immunizing a guinea pig with the crystal protein of the SDS502.

BEST MODE FOR CARRYING OUT THE INVENTION

Hereinafter, the present invention will be illustrated by way of Examples. However, the present invention is by no means limited by the following Examples.

EXAMPLE 1

Isolation of *Bacillus thuringiensis serovar galleriae* SDS502 Strain

From soil collected in the city of Tsukuba, a *Bacillus thuringiensis serovar galleriae* SDS502 strain was isolated by use of the following technique.

10 mg of sample soil was charged in an Erlenmeyer flask and 10 ml of sterilized water was poured therein. After shaking for 30 minutes, the mixture was left to stand for a while. Then, 2 ml of supernatant was taken out and immediately heated at 80° C. for 10 minutes. The heated liquid was diluted in two stages to 10 folds and further to 100 folds. 1 ml each of dilutions was incubated on an NB plate medium (0.3% of meat extract, 1.0% of peptone, 10.5% of NaCl, 2% of agar, pH 7.0/distilled water) at 30° C. for 24 to 48 hours.

Out of the obtained colonies, white, rough-edged and rapidly growing colonies were selected to obtain *Bacillus thuringiensis* in a high probability.

EXAMPLE 2

Bacteriological Properties of *Bacillus thuringiensis serovar galleriae* SDS502 Strain Method: Search was conducted in accordance with the taxonomy and bacteriological techniques described in Cowan. S. T., "Manual of Identification of Medical Bacteria" (translated by T. Sakazaki, Kindai Shuppan).

Figure 2:
FIG. 2 is a diagram illustrating the results of SDS-PAGE of crystal protein having a pesticidal activity of the present invention. 1 designates markers, showing 200, 116.25, 97.4, 66.2, and 45.0 kDa from the top. 2 represents the results of crySDS502 gene product expressed in *Escherichia coli*. 3 represents the results of SDS 502 crystal protein.
Figure 3:
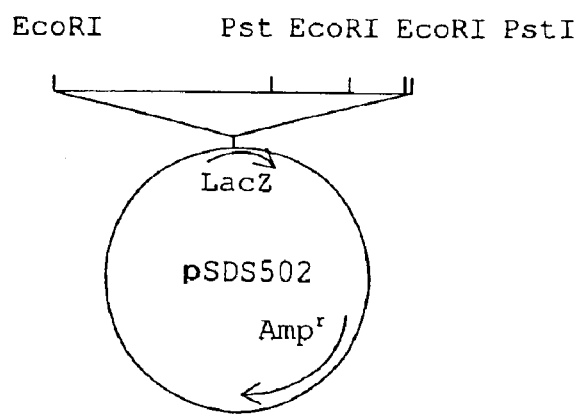
FIG. 3 is a diagram illustrating linkage of *Bacillus thuringiensis serovar galleriae* SD502 gene to a vector (gene cassette).

Gram stain: Gram-positive rod,

Morphology of colony: Forms an opaque beige colony having irregular edges,

Spore forming ability and shape of spore: (+) oval spore;

Catalase: (+),

Width of vegetative cell: 0.9 μ or more,

Production of AMC: (+),

Respiration: Facultative an aerobic,

Assimilation of D-Mannitol: (−),

Existence of crystal protein: (+),

Serum type of flagella: H anti-serum type (5a5b),

Cell contents: Spore forming cells produce amorphous type crystal protein (cf. FIG. 1), Alkali-soluble protein: (+) protein electrophoresed near 130 kDa (cf. FIG. 2), Activity: The strain of the invention has lethal activity on *Coleoptera* pests tested.

From the above findings, the strain of the invention was judged to be a novel strain. This was named *Bacillus thuringiensis serovar galleriae* SDS502 and deposited on Jul. 27, 2000, at Laboratory of Microbial Industry and Technology, Institute of Industrial Science Technology, Ministry of International Trade and Industry, (now National Institute of Advanced Industrial Science and Technology, Independent Administrative Institution) at AIST Tsukuba Central 6, 1-1, Higashi 1-Chome, Tsukuba-shi, Ibaraki-ken 305-8566 Japan under Accession No. FERM P-17979 and transferred to International Deposition under International Receipt No. FERM BP-7667.

EXAMPLE 3

Identification of Subtype of *Bacillus thuringiensis serovar galleriae* SDS502 Strain By use of an antibody to a protein of the flagellum of a serotyping *Bacillus* prepared with an antibody derived from an antigen of flagellum, an antigen-antibody reaction was carried out using a flagellum protein of an unknown bacterium as an antigen.

Flagellum H serum was prepared by heating the bacteria cells at 100° C. to peel flagella off. Using 40 kinds (subtypes) of H antigen standard strains of *Bacillus thuringiensis* that are already known, bacteria having good mobility were selected using a Craigie tube (0.5% semi-fluid agar medium) and formalized dead bacteria were prepared from them. The formalized dead bacteria were given to a rabbit to immunize it. H serum was prepared by absorbing a corresponding antibody to the *Bacillus thuringiensis* cell antigen from each antiserum. The serum type of H antigen and agglutinin value of the antibody were identified and quantitatively determined according to the method of Ooba and Ayusawa (I. Invertebr. Pathol., 32, 303–309, 1978).

The H antigen to *Bacillus thuringiensis serovar galleriae* SDS502 strain specifically agglutinates *serovar galleriae* only. The agglutinin value of *serovar galleriae* SDS502 strain H antiserum to a corresponding homo antigen was 12,800 folds and the agglutinin value of it to *serovar galleriae* HD8 strain (standard strain) was 6,400 folds. Therefore, SDS502 strain and *serovar galleriae* were judged to be the same strain.

EXAMPLE 4

Purification of Crystal Protein of SDS502 Strain and Properties Thereof

One platinum loop of SDS502 strain cells were taken out and inoculated in a test tube containing common bouillon medium (0.3% of meat extract, 1.0% of peptone, 0.5% of NaCl, pH 7.0/distilled water). Reciprocating shaking culture of it was performed at 30° C. for 24 hours to obtain a seed culture solution. The seed culture was inoculated in a 500 ml Erlenmeyer flask containing 100 ml of the above-mentioned medium such that the seed culture was in a final concentration of 1% and rotation shaking culture was performed at 30° C. for 96 hours at 250 rpm. Then, cells, spores and crystal protein were recovered by centrifugation. A suitable amount of buffer (Tris-HCl (Tris(hydroxymethyl)aminomethane Hydrochloride), NaCl, EDTA) was added to the obtained precipitate and supersonic destruction was performed to obtain a suspension. The obtained suspension was subjected to 8% SDS-PAGE gel electrophoresis to examine its electrophoretic pattern. Also, using an antibody, Western blotting was performed. As result, it was confirmed that there existed a crystal protein having molecular weight of about 130 kDa produced by the SDS502 strain.

EXAMPLE 5

Pesticidal Activity of SDS502 Strain on *Anomala cuprea, Popillia japonica, Anomala orientals, Plutella xylostella* and *Bombyx mori*.

The suspension prepared in Example 4 was diluted to a crystal protein concentration of 10 μg/ml and a spreading agent was added thereto to obtain a sample solution. The sample solution was mixed with leaf mold that had been subjected to sterilization treatment in advance and 1st stage, 2nd stage and 3rd stage larvae of *Anomala cuprea*, 1st stage and 2nd stage larvae of *Popillia japonica*, as well as 1st stage and 2nd stage larvae of *Anomala orientalis* were released.

Furthermore, the leaf of cabbage was dipped in the sample solution and thereafter it was sufficiently air-dried. This was placed in a Styrol cup containing wet filter paper. In the cup, larvae of *Plutella xylostella* in the middle phase of 3rd stage were released. After 7 days (after 5 days in the case of *Bombyx mori*, or after 2 days in the case of *Plutella xylostella*), the mortality of larvae was obtained according to the following formula. The tests were performed in 5 series with 5 insects per lot.

Mortality (%)=(Number of dead insect/Number of released insect)×100

Furthermore, the sample solution mixed with 5 g of artificial feed stuff was charged in a dish. In the dish, larvae of *Bombyx mori* on the 2nd day in the 3rd stage were released and the mortality of larvae after 7 days (after 5 days in the case of *Bombyx mori*, or after 2 days in the case of *Plutella xylostella*) was obtained according to the above-mentioned formula. The tests were performed in 5 series with 5 insects per lot. As a control, a test solution of the pesticidal protein produced by *Bacillus thuringiensis serovar galleriae* HD8 strain (standard strain) was prepared in the same manner as above and comparison therewith was made.

As a result, as indicated in the pesticidal spectrum of the crystal protein produced by *Bacillus thuringiensis serovar galleriae* SDS502 strain (Table 1), the pesticidal protein produced by the SDS502 strain exhibited pesticidal effect to *Anomala cuprea* Hope, *Anomala orientalis*, and *Popillia japonica* belonging to *Coleoptera* in a concentration of 10 μg/ml while the crystal protein produced by *Bacillus thuringiensis serovar galleriae* HD8 strain (standard strain) exhibited no pesticidal effect. On the other hand, the HD8 strain (standard strain) exhibited high activity to larvae of

*Bombyx mori*, *Plutella xylostella*, and *Spodoptera litura* belonging to Lepidoptera while the SDS502 strain exhibited no activity to Lepidoptera insects except for *Plutella xylostella*. These results suggest that the crystal proteins have different compositions and the strains cannot be said to be completely the same strain in consideration of the facts that the *galleriae* standard strain has cry1Ab gene and exhibits a pesticidal effect to Coleoptera while the SDS502 strain exhibits substantially no pesticidal activity to Lepidoptera.

TABLE 1

Mortality (%) After 7 Days From Eating Crystal Protein 10 μg)

| Name of Insect | Bacillus thuringiensis serovar galleriae | |
|---|---|---|
| | SDS 502 Strain | HD8 Strain (Standard Strain) |
| Anomala cuprea larvae (1st stage Larvae) | 100 | 0 |
| Anomala cuprea larvae (2nd stage Larvae) | 100 | 0 |
| Anomala cuprea larvae (3rd stage Larvae) | 80 | 0 |
| Popillia japonica (1st stage Larvae) | 100 | 0 |
| Popillia japonica (2nd stage Larvae) | 100 | 0 |
| Anomala orientalis larvae (1st stage Larvae) | 100 | 0 |
| Anomala orientalis larvae (2nd stage Larvae) | 100 | 0 |
| Bombyx mori* | 0 | 80 |
| Plutella xylostella** | 40 | 80 |
| Spodoptera litura | 0 | 40 |

*Examiner after 5 days; **Examiner after 2 days

EXAMPLE 6

Gene Relating to Pesticidal Protein of *Bacillus thuringiensis serovar galleriae* SDS502 Strain An antibody obtained by immunizing a guinea pig with about 130 kDa crystal protein produced by *Bacillus thuringiensis serovar galleriae* SDS502 strain was used for cloning a gene encoding SDS502 strain crystal protein (hereinafter, abbreviated as SDS502 gene). The cloned gene had 3,690 nucleotides and contained a translation region ranging from 187th ATG codon to 3,688th TAA codon. Further, it was compared with known genes, i.e., *japonensis buibui* gene (Japanese Patent Application Laid-open No. H6-65292) and *japonensis* N141 gene (Japanese Patent Application Laid-open No. H8-228783) effective to *Coleoptera* insects. As a result, it revealed that the both genes showed only 71% and 42% homologies, respectively, in amino acid sequence.

EXAMPLE 7

Isolation and Cloning of SDS502 Gene

Total DNA was prepared from SDS502 strain and partially cleaved with restriction enzyme EcoRI. From the cleaved DNA, about 2 to 5 kbp DNA fragment was obtained by fractionation and ligated with a phage vector (λgt11) cleaved with EcoRI. *Escherichia coli* was transformed with the product. Then, the recombinant *Escherichia coli* clone was subjected to antibody screening with an antibody obtained by immunizing a guinea pig with the about 130-kDa protein that was considered to be SDS502 stain crystal protein to identify a clone containing the SDS502 gene. DNA was prepared from the recombinant *Escherichia coli* clone and the DNA was cleaved with restriction enzyme EcoRI. The cleaved DNA fragments were electrophoresed on 0.8% agarose gel to identify an about 3.4-kbp insert DNA fragment.

The obtained DNA fragment was fractionated and ligated to Bluescript II SK(−), which was a plasmid vector cleaved with EcoRI, to prepare a gene cassette (pSDS502) (FIG. 3). Since this pSDS502 was not of full length, cloning was performed again to obtain a full-length pSDS502. Thereafter, the nucleotide sequence of the DNA fragment containing full-length SDS502 gene was determined by dideoxy method.

EXAMPLE 8

Expression SDS502 Crystal Protein in *Escherichia coli* (*E. coli*:DH5α) and Properties of Expressed Protein To produce crystal protein using the SDS502 gene, *Escherichia coli* (*E. coli*: DH5α) was transformed by use of the gene cassette (pSDS502) to obtain a recombinant *Escherichia coli* (hereinafter referred to as *E. coli*:DH5α (pSDS502)). The recombinant *Escherichia coli* was incubated in LB-amp liquid medium (10 g of Trypton, 10 g of NaCl, 5 g of yeast extract, 0.2% of glucose, 50 mg/l of sterilized water of ampicillin) at 37° C. for about 3 hours. Then, isopropyl 1-thio-β-D-galactoside (IPTG) was added thereto to a final concentration of 1 mM and the cultivation was continued for additional 20 hours at 37° C. After completion of the cultivation, the culture was centrifuged. Lysisbuffer was added to the precipitate in an amount of 4 folds (W/V) and the mixture was suspended at room temperature for 10 minutes. Then Lysozyme was added thereto to a final concentration of 1 mg/ml and after mixing, the mixture was left to stand on ice for 10 minutes. Further, TRITON™ X-100 Surfactant was added to this to a final concentration of 1% and after mixing, the mixture was centrifuged and the supernatant portion thereof was recovered. The obtained supernatant was subjected to 8% SDS-PAGE gel electrophoresis to examine its electrophoretic pattern. Also, Western blotting by use of an antibody was performed. As a result, it was observed that *E. coli*:DH5α (pSDS502) produced a crySDS502 crystal protein.

EXAMPLE 9

Pesticidal Activity of Crystal Protein Derived from *E. coli*:DH5α(pSDS502) on 1st stage larvae of *Anomala cuprea* and of *Popillia japonica*

The supernatant solution obtained as described above was diluted such that the concentration of crystal protein was 10 μg/ml and a spreading agent was added thereto to make a sample solution. The sample solution was mixed with leaf mold that had been subjected to sterilization treatment in advance and 1st stage larvae of *Anomala cuprea* and of *Popillia japonica*, were released. As a result, it was confirmed that the sample solution exhibited pesticidal activity on *Anomala cuprea* and *Popillia japonica*.

INDUSTRIAL APPLICABILITY

According to the present invention, a novel microbe *Bacillus thuringiensis serovar galleriae* SDS502 strain having ability of producing a toxic protein having high pesticidal activity on *Coleoptera* larvae has been found out and also a gene encoding the pesticidal crystal protein and pesticidal crystal protein have been found out. Furthermore, by formulating a noxious organism-controlling agent comprising the protein as an active ingredient, a noxious organism-controlling agent having activity on noxious organisms that have acquired a resistance to the conventional Bt can be provided. In particular, the noxious organism-controlling agent of the present invention is superior in effect on larvae of *Anomala cuprea*, which is a strong pest for lawn grasses, taro, sweet potato, peanut and so forth, and on *Anomala orientalis* and *Popillia japonica* and so forth, which are pests for lawn grasses, with better cost performance, as compared with the conventional pesticides produced by chemical synthesis and the *buibui* strain belonging to the subgenus *japonensis*.

---

What is claimed is:

1. An isolated protein comprising the amino acid sequence of SEQ ID NO: 1, wherein said protein exhibits a pesticidal activity.

2. A method for controlling a noxious organism, comprising feeding to a noxious organism a protein of claim 1 to protect a plant from damage caused by said noxious organism.

3. The method for controlling a noxious organism of claim 2, wherein said noxious organism is a *Coleoptera* insect.

4. A noxious organism-controlling agent, comprising:
   (a) a microbe that produces a protein having the amino acid sequence of SEQ ID NO: 1, wherein said microbe is selected from the group consisting of:
   (1-1) *Bacillus thuringiensis* serovar *galleriae* SDS502 strain,
   (1-2) a mutant of *Bacillus thuringiensis* serovar *galleriae* SDS502 strain, and
   (1-3) a microbe transformed with a polynucleotide comprising a nucleotide sequence encoding a protein comprising the amino acid sequence of SEQ ID NO: 1, or
   (b) a protein having the amino acid sequence of SEQ ID NO: 1 and having a pesticidal activity.

5. An isolated *Bacillus thuringiensis* serovar *galleriae* SDS502 strain that produces a protein having the amino acid sequence of SEQ ID NO: 1 that exhibits a pesticidal activity.

* * * * *